(12) United States Patent
Matsumoto et al.

(10) Patent No.: US 9,063,036 B2
(45) Date of Patent: Jun. 23, 2015

(54) SAMPLE FOR ELECTRON MICROSCOPY AND METHOD OF MANUFACTURING THE SAME

(71) Applicant: HONDA MOTOR CO., LTD., Tokyo (JP)

(72) Inventors: Kenji Matsumoto, Wako (JP); Hideo Watanabe, Fukuoka (JP)

(73) Assignee: HONDA MOTOR CO., LTD., Tokyo (JP)

( * ) Notice: Subject to any disclaimer, the term of this patent is extended or adjusted under 35 U.S.C. 154(b) by 37 days.

(21) Appl. No.: 13/934,225

(22) Filed: Jul. 3, 2013

(65) Prior Publication Data
US 2014/0026672 A1     Jan. 30, 2014

(30) Foreign Application Priority Data

Jul. 25, 2012  (JP) .................. 2012-164770

(51) Int. Cl.
| | |
|---|---|
| G01N 3/02 | (2006.01) |
| G01L 1/04 | (2006.01) |
| G01N 3/62 | (2006.01) |
| H01J 37/20 | (2006.01) |
| H01J 37/26 | (2006.01) |

(52) U.S. Cl.
CPC .. *G01N 3/02* (2013.01); *G01N 3/62* (2013.01); G01N 2203/0017 (2013.01); G01N 2203/0286 (2013.01); G01N 2203/0617 (2013.01); G01N 2203/0647 (2013.01); *H01J 37/20* (2013.01); *H01J 37/26* (2013.01); H01J 2237/206 (2013.01); H01J 2237/24585 (2013.01)

(58) Field of Classification Search
CPC ............ G01N 2203/0286; G01N 3/08; G01N 2223/307; G01N 2203/0017; G01N 2203/0617; G01N 2203/0647; G01N 2203/037; G01N 3/02; G01N 3/62; B82Y 35/00
USPC ............... 73/856, 774–775, 864.91; 250/311, 250/440.11
See application file for complete search history.

(56) References Cited

U.S. PATENT DOCUMENTS

| | | | | |
|---|---|---|---|---|
| 6,817,255 | B2 * | 11/2004 | Haque et al. | 73/862.638 |
| 7,586,105 | B2 * | 9/2009 | Molhave | 250/440.11 |
| 8,069,733 | B2 * | 12/2011 | Han et al. | 73/781 |
| 8,294,098 | B2 * | 10/2012 | Zhang et al. | 250/311 |
| 8,302,494 | B2 * | 11/2012 | Han et al. | 73/862.634 |
| 8,569,714 | B2 * | 10/2013 | Han et al. | 250/440.11 |
| 2002/0194938 | A1 * | 12/2002 | Koo et al. | 73/864.91 |
| 2006/0289784 | A1 * | 12/2006 | Deguchi et al. | 250/441.11 |

FOREIGN PATENT DOCUMENTS

| | | |
|---|---|---|
| JP | 2506064 B2 | 10/1986 |
| JP | 2010-44999 | 2/2010 |
| JP | 2011-106883 | 6/2011 |

* cited by examiner

*Primary Examiner* — Lisa Caputo
*Assistant Examiner* — Jonathan Dunlap
(74) *Attorney, Agent, or Firm* — Mori & Ward, LLP (57) ABSTRACT

A sample for electron microscopy includes a base member and a sensor. The sensor is configured to measure data on the sample. The sensor includes an insulating member and a measuring element. The insulating member is deposited in or near an area of observation that is defined on a surface of the base member. The measuring element is deposited on a surface of the insulating member or over the surface of the base member and the surface of the insulating member.

19 Claims, 6 Drawing Sheets

SAMPLE FOR ELECTRON MICROSCOPY AND METHOD OF MANUFACTURING THE SAME

CROSS-REFERENCE TO RELATED APPLICATIONS

The present application claims priority under 35 U.S.C. §119 to Japanese Patent Application No. 2012-164770, filed Jul. 25, 2012, entitled "Sample for Electron Microscopy and Method of Manufacturing the Same." The contents of this application are incorporated herein by reference in their entirety.

BACKGROUND OF THE INVENTION

1. Field of the Invention

The present application relates to a sample for an electron microscope and a method of manufacturing the sample.

2. Discussion of the Background

Observation of a sample (specimen) through an electron microscope such as a TEM or a SEM is sometimes conducted while data such as the stress occurring in the sample or the temperature of the sample are measured. In the related art, particularly in researches on nuclear energy and other fields, the strain (stress) occurring in a sample for electron microscopy is measured by measuring changes in the position of a mark provided on a surface of the sample by means of laser processing or the like. According to this method, since the amount of strain is measurable while the mark is observed through an electron microscope, the accuracy in the measurement of the amount of strain is relatively high. Instead, the necessity of providing the mark on the surface of the sample makes the manufacturing of the sample troublesome and time-consuming. Moreover, it takes time to analyze the results of the measurement. Therefore, the above method is not very suitable for simple measurement of strain occurring in the sample.

A related-art method disclosed in Japanese Unexamined Patent Application Publication No. 2011-106883, for example, employs a sample holder on which a sample is subjected to a tension test during an observation conducted through a TEM. In this method, the sample, which is a thin plate, is fastened to the sample holder with a pair of fastening tools (fixing screws) provided in a fixed tool and a movable tool, respectively. The fastening tools are screwed in a pair of holes, respectively, provided in the sample. One end of the sample thus held is pulled by moving the movable tool in a direction away from the fixed tool so that the sample is stretched. In this state, the sample is observed through a TEM while a tensile load thus produced is measured.

In the above sample holder, the stress occurring in or near an area of observation of the sample is measured by measuring the tensile load applied to the movable tool included in the sample holder. In this method, however, the stress occurring in the sample is not directly measured. Therefore, the measurements tend to include errors depending on the strength with which the sample is fixed to the sample holder, the elastic force of the sample holder itself, the extent of deterioration of the sample holder, and other factors.

Moreover, in the above sample holder, the direction in which the tensile load is applied to the sample holder is not necessarily the same as the direction in which the stress (strain) occurs in or near the area of observation of the sample. Practically, the direction in which the stress occurs is often angled with respect to the direction in which the tensile load is applied to the sample holder. Consequently, the stress (strain) in or near the area of observation of the sample generated by the tension applied to the sample might not be measured accurately.

To accurately measure data such as the stress occurring in the sample for electron microscopy or the temperature of the sample, it is desirable to attach, directly to the sample, an element such as a stress sensor (strain gauge) or a temperature sensor (thermocouple) that is capable of measuring data such as the stress occurring in the sample or the temperature of the sample in or near the area of observation of the sample. Nevertheless, since a sample intended for a TEM, for example, has as small diameter as about 3 mm and as small thickness as about 30 µm to 50 µm, it is impossible in the related-art method to attach a measuring element such as a strain gauge or a temperature sensor to the sample. Hence, as disclosed by Japanese Patent No. 2506064, for example, a strain gauge is usually attached to a surface of an object of measurement with adhesive. In such a case, the hardness or bonding strength of the adhesive may affect the measurements of the strain. Accordingly, if a strain gauge is attached to a very thin sample such as a sample intended for observation through a TEM, it is quite likely that the measurements may include errors exceeding the tolerance. Moreover, attaching such a very small strain gauge to a sample with adhesive requires a high level of skill, and only limited workers have such skill. That is, such a method is not practical.

SUMMARY OF THE INVENTION

According to one aspect of the present invention, a sample for electron microscopy includes a base member and a sensor. The sensor is configured to measure data on the sample. The sensor includes an insulating member and a measuring element. The insulating member is deposited in or near an area of observation that is defined on a surface of the base member. The measuring element is deposited on a surface of the insulating member, or over the surface of the base member and the surface of the insulating member.

According to another aspect of the present invention, in a method of manufacturing a sample for electron microscopy, a sensor is provided on a surface of the sample. The sensor is configured to measure data on the sample. In the providing of the sensor, an insulating member is deposited in or near an area of observation that is defined on a surface of a base member included in the sample, and a measuring element is deposited on a surface of the insulating member or over the surface of the base member and the surface of the insulating member.

According to further aspect of the present invention, in a method of manufacturing a sample for electron microscopy, an insulating member is deposited in or near an area of observation that is defined on a surface of a base member included in the sample. A measuring element is deposited on a surface of the insulating member, or over the surface of the base member and the surface of the insulating member to provide a sensor on a surface of the sample. The sensor is configured to measure data on the sample.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings.

DESCRIPTION OF THE EMBODIMENTS

The embodiments will now be described with reference to the accompanying drawings, wherein like reference numerals designate corresponding or identical elements throughout the various drawings.

Figure 1A:
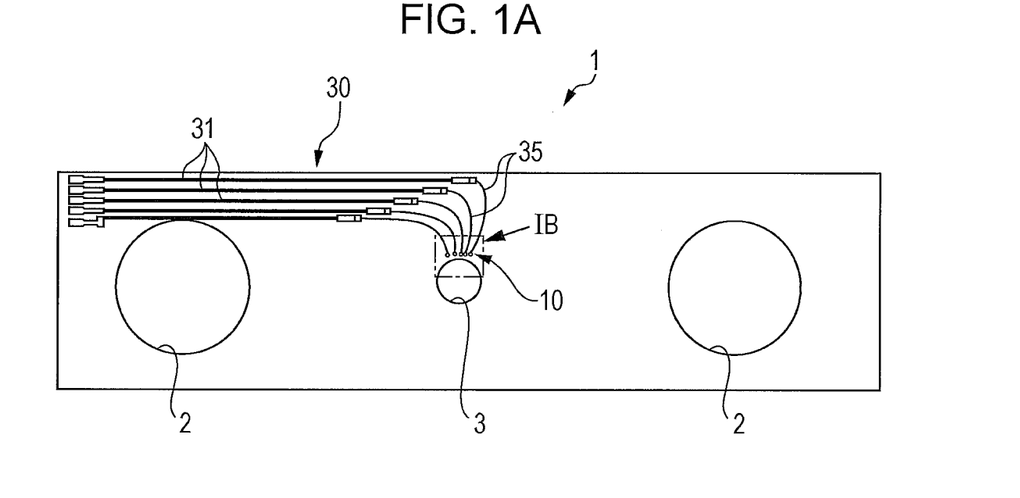
FIG. 1A is a plan view illustrating the entirety of a sample, intended for a TEM, according to a first embodiment of the present application to which stress sensors are attached.
Figure 1B:
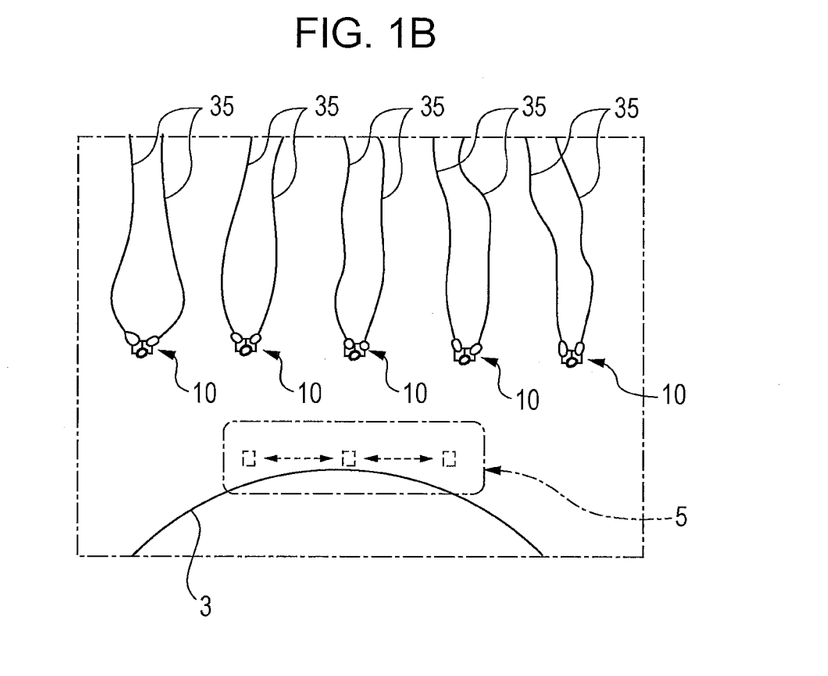
FIG. 1B is an enlargement of part IB illustrated in FIG. 1A.
Figure 2:
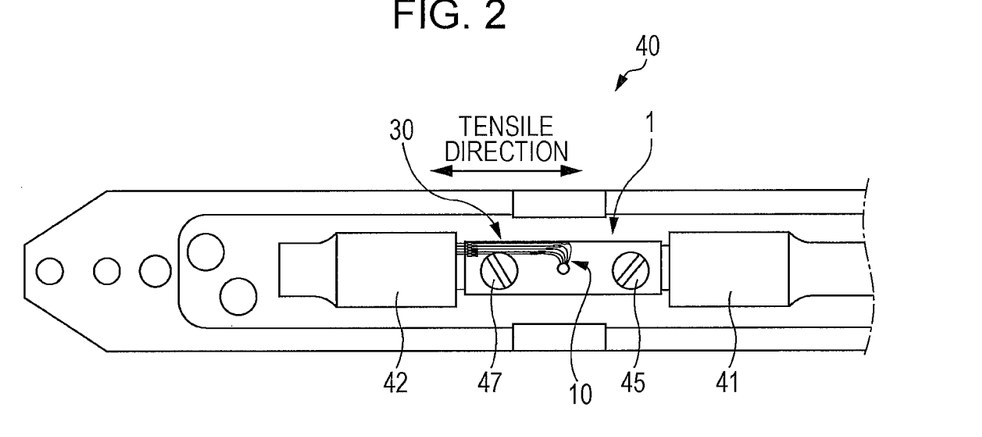
FIG. 2 illustrates part of a sample holder configured to hold the sample.

FIGS. 1A and 1B illustrate a sample (specimen) 1, intended for a TEM, according to a first embodiment of the present application to which stress sensors 10 are attached. FIG. 1A is a plan view illustrating the entirety of the sample 1. FIG. 1B is an enlargement of part IB illustrated in FIG. 1A. FIG. 2 illustrates part of a sample holder 40 configured to hold the sample 1. The sample 1 illustrated in FIGS. 1A and 1B is to be subjected to a tension test during an observation conducted through a TEM. The sample 1 is a thin plate-like member having a substantially oblong rectangular contour. The sample 1 has a pair of fixing holes (screw holes) 2 provided near two ends in the longitudinal direction thereof and into which a pair of fixing screws 45 and 47 provided on the sample holder 40 illustrated in FIG. 2 are to be screwed, respectively.

The sample holder 40 is to be set in a sample chamber (not illustrated) of the TEM while holding the sample 1. In the sample chamber, a tensile load can be applied to the sample 1. To do so, the sample holder 40 includes a movable tool 41, a fixed tool 42, and the pair of fixing screws 45 and 47 fitted in the movable tool 41 and the fixed tool 42, respectively. The movable tool 41 is movable in a direction away from the fixed tool 42. The pair of fixing screws 45 and 47 fitted in the movable tool 41 and the fixed tool 42 are screwed into the pair of fixing holes 2 provided in the sample 1, whereby the sample 1 is held by the sample holder 40. In this state, the movable tool 41 is moved such that one end of the sample 1 is pulled. While the sample 1 is thus stretched in the longitudinal direction thereof, the sample 1 is observed through the TEM.

Figure 3A:
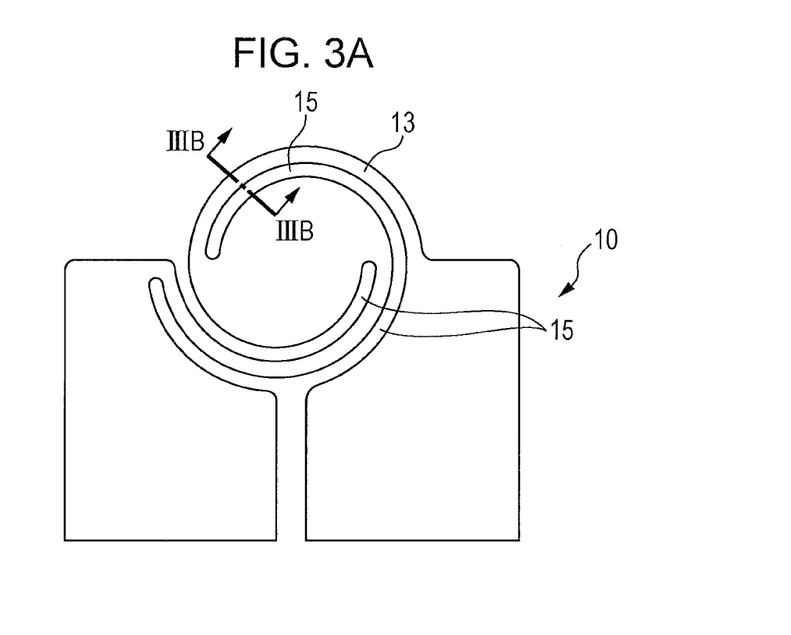
FIG. 3A is a plan view of one of the stress sensors attached to the sample.
Figure 3B:
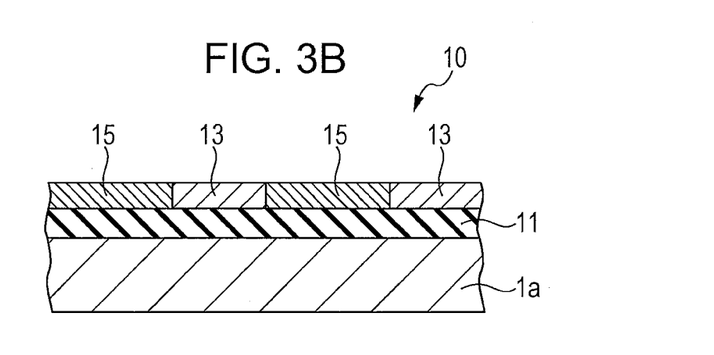
FIG. 3B is a sectional view taken along line IIIB-IIIB illustrated in FIG. 3A and seen in the direction of the arrows illustrated in FIG. 3A.

As illustrated in FIG. 1A, a circular through hole 3 is provided in the center of the sample 1. As illustrated in FIG. 1B, a surface of observation (area of observation) 5 to be observed through the TEM is defined in a portion along the circumference of the through hole 3. The surface of observation 5 of the sample 1 has a thickness of about 30 μm to 50 μm, for example. The through hole 3 and the surface of observation 5 are provided by a known method such as electropolishing. The stress sensors 10 are provided on the sample 1 near the surface of observation 5. FIGS. 3A and 3B illustrate details of one of the stress sensors 10. FIG. 3A is a plan view. FIG. 3B is a sectional view taken along line IIIB-IIIB illustrated in FIG. 3A and seen in the direction of the arrows illustrated in FIG. 3A. As illustrated in FIG. 3B, each stress sensor 10 includes an insulating member 11 deposited on a surface (the upper surface) of a base member 1a forming the sample 1, and a strain gauge element (measuring element) 13 deposited on a surface (the upper surface) of the insulating member 11. The insulating member 11 is made of ceramic or glass such as $Al_2O_3$ or $SiO_2$. The strain gauge element 13 may be a metal thin film made of an alloy (such as a Cu—Ni-based alloy, a Ni—Cr-based alloy, a Ag alloy, or a Ni alloy) that is used for a typical strain gauge. The strain gauge element 13, which is a film formed by deposition, is very thin with a thickness of 1 μm to 10 μm.

A portion on the surface of the insulating member 11 that is free of the strain gauge element 13 (a recess defined by the strain gauge element 13 provided on the insulating member 11) is covered with a filler member (recess-filling member) 15 deposited thereon so as to fill the recess in that portion. The filler member 15 is a thin film made of a nonmetallic material such as silicon or ceramic. As illustrated in FIG. 3B, the filler member 15 has substantially the same thickness as the strain gauge element 13 and adjoins the edges of the strain gauge element 13 with no gaps interposed therebetween.

As illustrated in FIG. 1A, a terminal unit (terminal) 30 that relays and extracts detection signals from the stress sensors 10 (strain gauge elements 13) to the outside is provided on the surface of the sample 1 (base member 1a). The terminal unit 30 includes insulating members 11 (see FIG. 3B) deposited on the surface of the base member 1a, and terminal elements 31 deposited on the surface of the respective insulating members 11 and made of an electrically conductive material. In the first embodiment, the insulating members 11 are provided only on portions of the surface of the sample 1 (base member 1a) where the stress sensors 10 and the terminal elements 31 are provided.

The terminal elements 31 are connected to the strain gauge elements 13, respectively, with lead wires 35. The lead wires 35 are thin wire members made of metal such as gold or copper. The two ends of each of the lead wires 35 are connected to a corresponding one of the terminal elements 31 and a corresponding one of the strain gauge elements 13, respectively, by a method such as wire bonding. The terminal elements 31 extend linearly from one corner (the upper left corner in FIG. 1A) on the upper surface of the sample 1 and along one side (the upper side in FIG. 1A) of the sample 1. One terminal element 31 is provided for each of the stress sensors 10. The terminal elements 31 are desired to be provided on a portion of the sample 1 as far from the surface of observation 5 as possible. While the first embodiment concerns an exemplary case where the terminal elements 31 of the terminal unit 30 extend from one corner of the sample 1 and along one side of the sample 1, the terminal elements 31 of the terminal unit 30 may alternatively be provided on any other portion of the sample 1 as long as measured data on the surface of observation 5 are not affected and can be extracted from that portion to the outside of the sample 1.

To attach the stress sensors 10 configured as described above to the sample 1, a mask (not illustrated) having a pattern of openings corresponding to the pattern of the insulating members 11 is first provided on a surface of the base member 1a. The mask may be a known photoresist layer or the like. In this state, films made of ceramic or glass and functioning as the insulating members 11 are deposited on the surface of the base member 1*a* by using a vacuum deposition apparatus (not illustrated). Subsequently, the mask is removed from the surface of the base member 1*a*. Then, another mask having a pattern of openings corresponding to the pattern of the strain gauge elements 13 is provided over the insulating members 11. In this state, films made of a Cu—Ni alloy or the like and functioning as the strain gauge elements 13 are deposited on the insulating members 11. Subsequently, the mask is removed from the surfaces of the insulating members 11. Then, yet another mask having a pattern of openings corresponding to the pattern of the filler members 15 is provided over the insulating members 11. In this state, films made of a Cu—Ni alloy or the like and functioning as the filler members 15 are deposited on portions of the surface of the insulating member 11 that are free of the strain gauge elements 13. Then, the mask is removed from the surfaces of the insulating members 11. In this manner, the formation of the insulating members 11, the strain gauge elements 13, and the filler members 15 by vacuum deposition is completed. The insulating members 11 and the terminal elements 31 that are included in the terminal unit 30 can be also formed by vacuum deposition, as with the stress sensors 10.

With the sample 1 according to the first embodiment that is provided with the stress sensors 10, the stress (strain) occurring in or near the surface of observation 5 of the sample 1 is directly measurable with the stress sensors 10 each including the insulating member 11 deposited on or near the surface of observation 5 of the base member 1*a* and the strain gauge element 13 deposited on the insulating member 11. Hence, the stress occurring in or near the surface of observation 5 of the sample 1 is measurable with extremely high accuracy. Furthermore, since the stress sensors 10 each include the insulating member 11 and the strain gauge element 13 that are deposited as very thin films each having a thickness of about several microns, the stress sensors 10 have no or only a negligible influence upon the results of measurement and observation even if the stress sensors 10 are attached to the small and very thin sample 1 intended for a TEM. Hence, observation of the sample 1 through a TEM can be conducted in a known manner, and the stress (strain) occurring in the sample 1 can be measured accurately.

Since the strain gauge elements 13 are formed by deposition, the flexibility in selecting the shape and the material of the strain gauge elements 13 is relatively high. Moreover, if the pattern of the mask used in the deposition of the strain gauge elements 13 is determined appropriately, the strain gauge elements 13 can be provided at a plurality of positions on the surface of the sample 1 (base member 1*a*). That is, the number of points of measurement on the sample 1 can be increased easily, enabling the measurement of stress distribution on the sample 1.

In the sample 1 including the stress sensors 10, since the insulating members 11 are formed by deposition, the insulating members 11 can have a certain strength with a small thickness on the surface of the base member 1*a*. Accordingly, the stress (strain) occurring with the deformation of the base member 1*a* is measurable accurately. Moreover, since the strain gauge elements 13 are provided as thin films, the speed of data measurement (response speed) is increased, enabling quick measurement of stress data.

In a known strain gauge, since an insulating member provided between an object of measurement and a base member is made of a synthetic resin material such as polyimide, data measurement cannot be conducted in an environment at a high temperature exceeding the heat-resistant temperature of the insulating member. In contrast, in each of the stress sensors 10 included in the sample 1 according to the first embodiment of the present application, since the insulating member 11 provided between the base member 1*a* and the strain gauge element 13 is made of ceramic or glass, the insulating member 11 is highly heat-resistant. Hence, the sample 1 can undergo observation and tests conducted in an environment at a high temperature.

The sample 1 includes the terminal unit 30 through which measurement signals generated by the strain gauge elements 13 are extracted to the outside. The terminal unit 30 includes the terminal elements 31 deposited on the surface of the sample 1. In such a configuration, since the terminal unit 30 through which measurement signals from the stress sensors 10 are extracted to the outside is provided on the sample 1, the measurement signals can be extracted from the terminal unit 30 to the outside of the sample 1 via lead wires (not illustrated).

The sample 1 also includes the filler members 15 deposited in and filling the recesses produced on portions of the insulating member 11 that are free of the strain gauge elements 13. That is, the recesses defined by the strain gauge elements 13 on the surfaces of the insulating members 11 are filled with the filler members 15. Hence, even if the base member 1*a* undergoes significant thermal expansion or deformation, the occurrence of displacement of the strain gauge elements 13 with respect to the base member 1*a* because of peeling or the like of the strain gauge elements 13 is effectively prevented. Accordingly, the stress (strain) caused by the deformation of the base member 1*a* can be measured more accurately.

Since the sample 1 according to the first embodiment is used in the sample chamber of a TEM that is in a vacuum state, there is no chance that the surfaces of the strain gauge elements 13 may be oxidized as long as the sample 1 is used normally. Accordingly, there is no need to provide an additional film such as an insulating film or a protective film over the strain gauge elements 13. In this respect also, the configuration of the stress sensors 10 is simplified.

A sample according to a second embodiment of the present application will now be described. In the description and drawings concerning the second embodiment, elements that are the same as or similar to those of the first embodiment are denoted by the corresponding reference numerals used in the first embodiment, and detailed description thereof is omitted. Factors that are not described below or illustrated in the relevant drawings are the same as those described in the first embodiment.

Figure 4A:
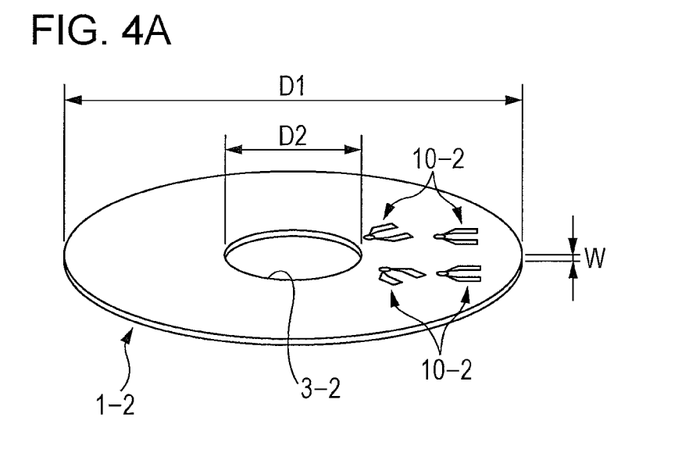
FIG. 4A is a schematic perspective view of a sample including temperature sensors according to a second embodiment of the present application.
Figure 4B:
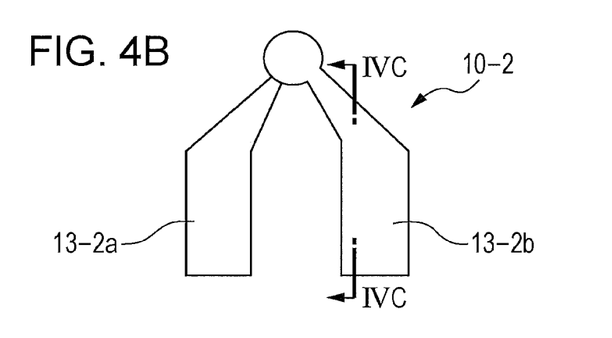
FIG. 4B illustrates one of the temperature sensors.
Figure 4C:
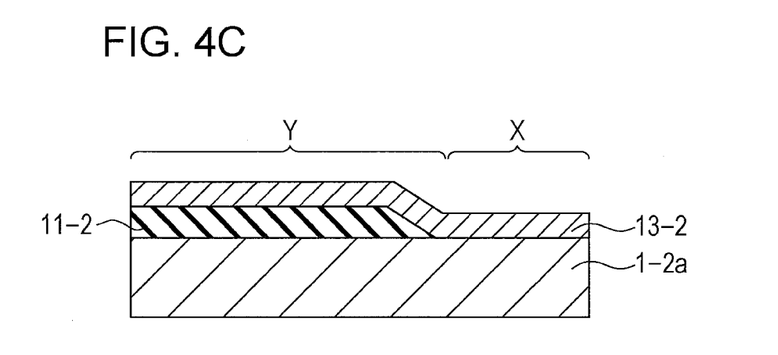
FIG. 4C is a sectional view taken along line IVC-IVC illustrated in FIG. 4B and seen in the direction of the arrows illustrated in FIG. 4B.

FIGS. 4A to 4C illustrate a sample 1-2 including temperature sensors 10-2 according to the second embodiment of the present application. FIG. 4A is a schematic perspective view of the sample 1-2 with the temperature sensors 10-2. FIG. 4B illustrates one of the temperature sensors 10-2. FIG. 4C is a sectional view taken along line IVC-IVC illustrated in FIG. 4B and seen in the direction of the arrows illustrated in FIG. 4B. As with the sample 1 according to the first embodiment, the sample 1-2 according to the second embodiment is intended for observation through a TEM. As illustrated in FIG. 4A, the sample 1-2 is an annular, thin plate-like member having a through hole 3-2 provided in the center thereof. For example, the sample 1-2 has a diameter D1 of about 3 mm, an inside diameter D2 of the through hole 3-2 of about 1 mm, and a thickness W of about 30 µm to 50 µm. As illustrated in FIG. 4B, each of the temperature sensors 10-2 attached to the sample 1-2 includes a thermocouple element (measuring element) 13-2 configured to measure the temperature of the sample 1-2. Specifically, as illustrated in FIG. 4C, the temperature sensor 10-2 includes an insulating member 11-2 deposited on the surface of a base member 1-2*a* forming the sample 1-2, and the thermocouple element (measuring element) 13-2 deposited over the surfaces of the insulating member 11-2 and the base member 1-2a. The thermocouple element 13-2 includes a positive-electrode element 13-2a and a negative-electrode element 13-2b. The positive-electrode element 13-2a and the negative-electrode element 13-2b may each be a thin film made of a material typically employed for a thermocouple (a material used for positive and negative electrodes of the thermocouple and represented by any of the following symbols: K, E, J, T, N, R, S, B, W/Re5-26, IrRh, CrAu, CuAu, and so forth).

As illustrated in FIG. 4C, the thermocouple element 13-2 according to the second embodiment extends over a portion X of the base member 1-2a that is free of the insulating member 11-2 and a portion Y of the base member 1-2a that is covered with the insulating member 11-2. A portion of the thermocouple element 13-2 extending on the portion X that is free of the insulating member 11-2 functions as a measuring portion with which the temperature of the base member 1-2a is measured. A portion of the thermocouple element 13-2 extending on the portion Y that is covered with the insulating member 11-2 functions as a wire portion that transmits, to the outside thereof, a measurement signal generated by the measuring portion.

Figure 5:
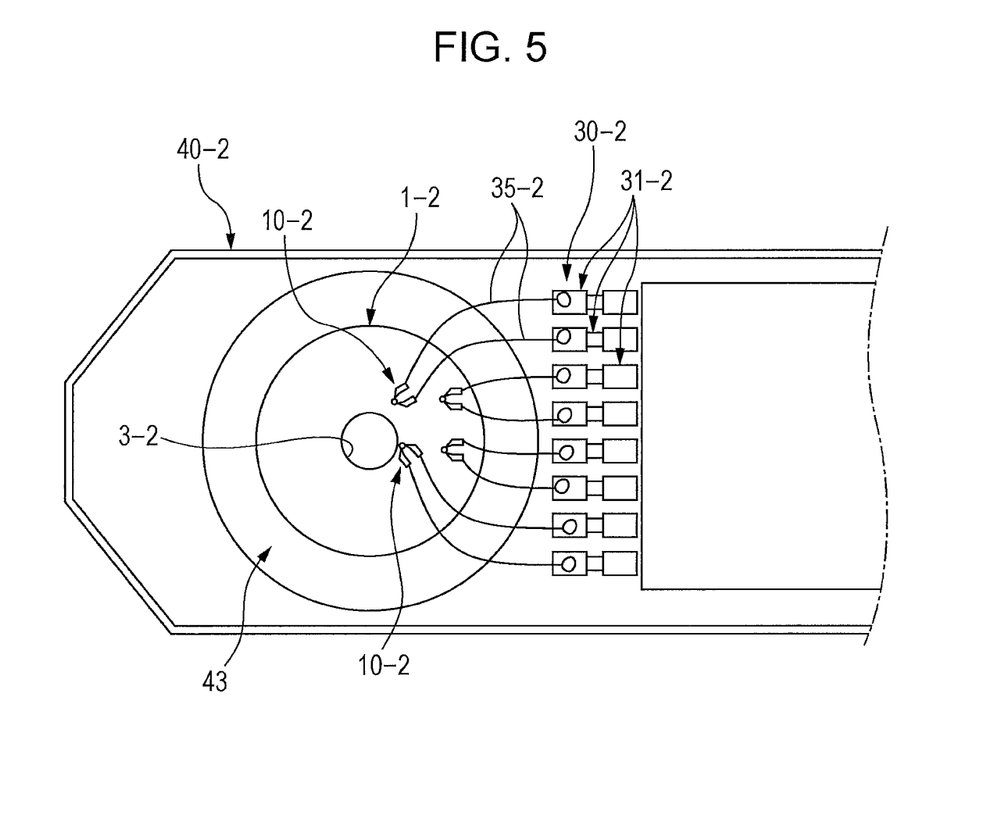
FIG. 5 illustrates part of a sample holder configured to hold the sample according to the second embodiment.

FIG. 5 is an enlarged view of a sample holder 40-2 configured to hold the sample 1-2 illustrating a part (the tip) thereof. The sample holder 40-2 illustrated in FIG. 5 includes a mounting portion 43 provided near the tip thereof and on which the sample 1-2 is mounted. The sample holder 40-2 also includes a terminal unit (terminal) 30-2 provided adjacent to the mounting portion 43 and through which measurement signals generated by the temperature sensors 10-2 (thermocouple elements 13-2) provided on the sample 1-2 are extracted to the outside. The terminal unit 30-2 includes terminal elements 31-2 provided on the surface (upper surface) of the sample holder 40-2 and made of an electrically conductive material. The terminal elements 31-2 are provided in a portion on the upper surface of the sample holder 40-2 that is adjacent to the mounting portion 43. The terminal elements 31-2 are provided in a plurality of pairs each including two elements provided for the positive-electrode element 13-2a and the negative-electrode element 13-2b, respectively, of a corresponding one of the temperature sensors 10-2 (thermocouple elements 13-2). The temperature sensors 10-2 (thermocouple elements 13-2) provided on the sample 1-2 mounted on the mounting portion 43 and the terminal elements 31-2 provided on the sample holder 40-2 are connected with lead wires 35-2. As with the lead wires 35 according to the first embodiment, the lead wires 35-2 are thin wire members made of metal such as gold or copper. One end of each of the lead wires 35-2 is connected to a corresponding one of the thermocouple elements 13-2 provided on the sample 1-2. The other end of each of the lead wires 35-2 is connected to a corresponding one of the terminal elements 31-2 provided on the sample holder 40-2. In addition, other lead wires (not illustrated) through which measurement signals generated by the thermocouple elements 13-2 are extracted to the sample holder 40-2 and to the outside of the TEM are connected to the terminal elements 31-2.

Figure 6A:
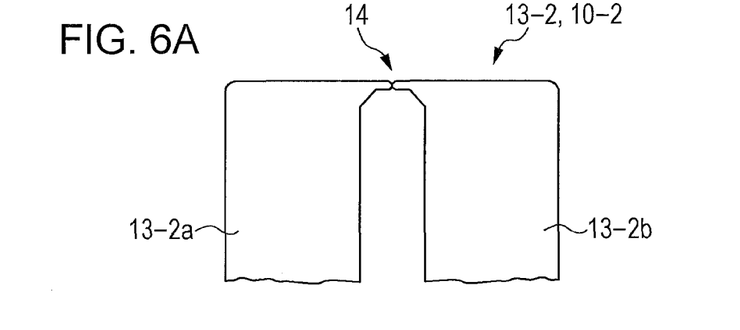
FIGS. 6A to 6C illustrate configurations of other types of exemplary measuring elements (thermocouple elements) included in the temperature sensors.
Figure 6B:
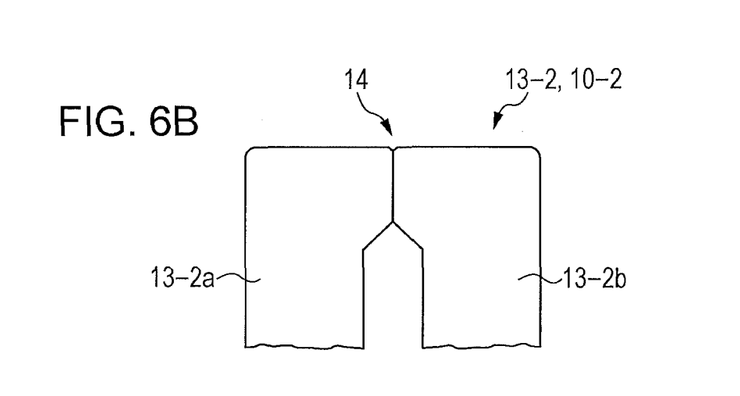
Figure 6C:
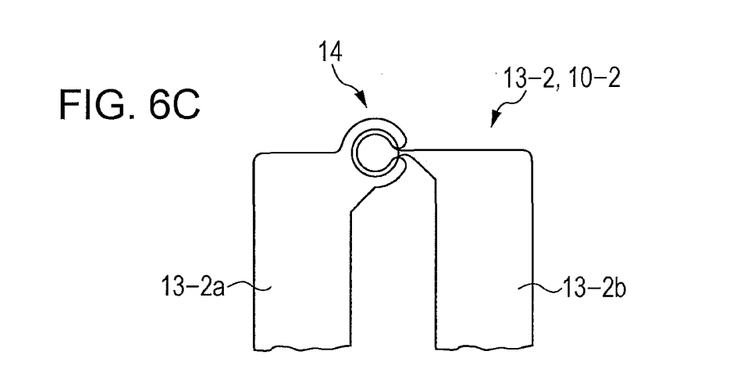

FIGS. 6A to 6C illustrate configurations of other types of exemplary thermocouple elements (measuring elements) 13-2 included in the temperature sensors 10-2. The thermocouple element 13-2 illustrated in FIG. 6A is a point-type thermocouple element in which a contact portion 14 between the positive-electrode element 13-2a and the negative-electrode element 13-2b provides a point contact. The thermocouple element 13-2 illustrated in FIG. 6B is a linear-type thermocouple element in which the contact portion 14 between the positive-electrode element 13-2a and the negative-electrode element 13-2b provides a linear contact. The thermocouple element 13-2 illustrated in FIG. 6C is a round-type thermocouple element in which the contact portion 14 between the positive-electrode element 13-2a and the negative-electrode element 13-2b provides an arc-shaped contact.

In the second embodiment also, the temperature of the sample 1-2 is directly measurable with the temperature sensors 10-2 each including the insulating member 11-2 deposited on the surface of the base member 1-2a and the thermocouple element 13-2 deposited over the surfaces of the insulating member 11-2 and the base member 1-2a. Hence, the temperature of the sample 1-2 is measurable with extremely high accuracy. Furthermore, since the temperature sensors 10-2 each include the insulating member 11-2 and the thermocouple element 13-2 that are deposited as very thin films each having a thickness of about several microns, the temperature sensors 10-2 have no or only a negligible influence upon the results of measurement and observation even if the temperature sensors 10-2 are provided on the small and very thin sample 1-2 intended for a TEM. Hence, observation of the sample 1-2 through a TEM can be conducted in a known manner, and the temperature of the sample 1-2 can be measured accurately.

Since the thermocouple elements 13-2 are formed by deposition, the flexibility in selecting the shape and the material of the thermocouple elements 13-2 is relatively high. Moreover, since the thermocouple elements 13-2 are formed by deposition, the thermocouple elements 13-2 can be provided at a plurality of positions on the surface of the sample 1-2 (base member 1-2a). That is, the number of points of measurement on the sample 1-2 can be increased easily, enabling the measurement of temperature distribution on the sample 1-2.

In the second embodiment, the terminal unit 30-2 through which measurement signals generated by the temperature sensors 10-2 (thermocouple elements 13-2) are extracted to the outside are attached to the sample holder 40-2. In such a configuration, since the terminal unit 30-2 through which the measurement signals generated by the temperature sensors 10-2 are extracted to the outside of the sample 1-2 is attached to the sample holder 40-2, the sample 1-2 is easily attachable to and detachable from the sample holder 40-2.

That is, the temperature sensors 10-2 according to the second embodiment are configured such that signal lines extending from the temperature sensors 10-2 provided on the sample 1-2 are drawn to the outside of the TEM via the terminal unit 30-2 provided on the sample holder 40-2. Hence, the sample 1-2 is attachable to and detachable from the sample holder 40-2 for a plurality of times without giving any damage or the like to the temperature sensors 10-2.

While exemplary embodiments of the present application have been described above, the present application is not limited to thereto. Various modifications can be made to the above embodiments within the technical scope of the appended claims and the description given in this specification referring to the accompanying drawings. For example, the shapes, dimensions, and other parameters of the samples 1 and 1-2 according to the above embodiments are only exemplary, and the sample including the sensor according to the present application is not limited to have such shapes, dimensions, and other parameters. Furthermore, while the above embodiments each concern a sample intended for observation through a TEM, the sample according to the present application is not limited thereto and may be a sample (specimen) intended for observation through any other electron microscope such as a SEM. Furthermore, the sensor attached to the sample according to the present application is not limited to a stress sensor or a temperature sensor as in each of the above embodiments and may be any other sensor (a pressure sensor or the like).

According to a first aspect of the embodiment, a sample (1) for electron microscopy includes a base member (1a), and a sensor (10) configured to measure data on the sample (1). The sensor (10) includes an insulating member (11) deposited in or near an area of observation (5) that is defined on a surface of the base member (1a), and a measuring element (13) deposited on a surface of the insulating member (11) or over the surface of the base member (1a) and the surface of the insulating member (11).

According to a second aspect of the embodiment, a method of manufacturing a sample (1) for electron microscopy includes forming a sensor (10) on a surface of the sample (1), the sensor (1) being configured to measure data on the sample (1). The forming of the sensor (10) includes depositing an insulating member (11) in or near an area of observation (5) that is defined on a surface of a base member (1a) included in the sample (1), and depositing a measuring element (13) on a surface of the insulating member (11) or over the surface of the base member (1a) and the surface of the insulating member (11).

With the sample for electron microscopy according to each of the above aspects of the embodiment, data such as the stress occurring in the sample or the temperature of the sample in or near the area of observation are directly measurable with the sensor including the insulating member deposited on or near the area of observation of the base member and the measuring element deposited on the surface of the insulating member or over the surfaces of the base member and the insulating member. Hence, the data on the sample in or near the area of observation are measurable with extremely high accuracy. Furthermore, since the sensor according to each of the above aspects of the embodiment includes the insulating member and the measuring element that are deposited as very thin films each having a thickness of about several microns, the sensor has no or only a negligible influence upon the results of measurement and observation even if the sensor is attached to such a small and very thin sample for electron microscopy. Hence, observation of the sample through an electron microscope can be conducted in a known manner, and data such as the stress occurring in the sample or the temperature of the sample can be measured accurately.

Since the measuring element is formed by deposition, the shape and the material of the measuring element is relatively flexibly selectable in accordance with the data, such as strain, temperature, or pressure, to be measured. Moreover, since the measuring element is formed by deposition, the measuring element can be provided at each of a plurality of positions on the surface of the sample (base member). That is, the number of points of measurement on the sample can be increased easily, enabling the measurement of stress distribution, temperature distribution, or the like on the sample.

In the sample according to each of the above aspects of the embodiment, since the insulating member is formed by deposition, the insulating member can have a certain strength with a small thickness on the surface of the base member. Accordingly, if the sensor is a stress (strain) sensor, the stress (strain) occurring with the deformation of the base member is measurable accurately. Alternatively, if the sensor is a temperature sensor, the temperature of the base member is measurable accurately. Moreover, since the measuring element is provided as a thin film, the speed of data measurement (response speed) is increased, enabling quick measurement of data such as strain and temperature.

In the above sample for electron microscopy, the insulating member (11) may be made of ceramic or glass. In a known strain gauge or the like, since an insulating member provided between an object of measurement and a base member is made of a synthetic resin material such as polyimide, data measurement cannot be conducted in an environment at a high temperature exceeding the heat-resistant temperature of the insulating member. In contrast, in the sensor included in the sample according to the each of the above aspects of the embodiment, since the insulating member provided between the base member and the measuring element is made of ceramic or glass, the insulating member is highly heat-resistant. Hence, the sample can undergo observation and tests conducted in an environment at a high temperature.

The above sample may further include a terminal unit (30) through which a measurement signal generated by the measuring element (13) is extracted to an outside, the terminal unit (30) including an insulating member (11) deposited on the surface of the base member (1a) and a terminal element (31) deposited on the surface of the insulating member (11). In such a configuration, since the terminal unit through which a measurement signal from the sensor is extracted to the outside is provided on the sample, the measurement signal can be extracted from the terminal unit to the outside of the sample via a lead wire or the like. Moreover, since the insulating member and the terminal element included in the terminal unit are both formed by deposition, the shapes and the materials thereof are highly flexibly selectable, as with the measuring element included in the above sensor. Hence, the terminal unit can be provided at any position on the sample at which the terminal unit does not affect the measured data obtained in the area of observation of the sample and from which the measured data can be easily extracted to the outside of the sample.

Alternatively, the above sample may further include a terminal unit (30-2) through which a measurement signal generated by the measuring element (13-2) is extracted to an outside, the terminal unit (30-2) including a terminal element (31-2) attached to a sample holder (40-2) configured to hold the sample (1-2) when observation through an electron microscope is conducted. In such a configuration, since the terminal unit through which the measurement signal from the sensor is extracted to the outside of the sample is attached to the sample holder, the sample is attachable to and detachable from the sample holder for a plurality of times without giving any damage or the like to the sensor, facilitating the data measurement conducted during the observation of the sample.

In the above sample, the sensor (10) may be a stress sensor (10) configured to measure a stress occurring in the sample (1), and a portion of the insulating member (11) that is free of the measuring element (13) may be provided with a recess-filling member (15) that is deposited thereon.

In such a configuration in which the recess-filling member is deposited on the portion of the insulating member that is free of the measuring element, even if the base member undergoes significant thermal expansion or deformation, the occurrence of displacement of the measuring element with respect to the base member because of peeling or the like of the measuring element is effectively prevented. Accordingly, the stress (strain) caused by the deformation of the base member can be measured more accurately.

Reference numerals with parentheses in the above description represent reference numerals given to the respective elements according to exemplary embodiments of the present application described above.

According to the above aspects of the embodiment concerning a sample for electron microscopy and a method of manufacturing the same, data such as the stress occurring in the sample or the temperature of the sample are directly measurable with a simple configuration. Therefore, highly accurate data measurement through a simple test or observation is realized.

Obviously, numerous modifications and variations of the present invention are possible in light of the above teachings. It is therefore to be understood that within the scope of the appended claims, the invention may be practiced otherwise than as specifically described herein.

What is claimed is:

1. A sample for electron microscopy, comprising:
   a base member; and
   a sensor configured to measure data on the sample, the sensor comprising:
      an insulating member deposited in or near an area of observation that is defined on a surface of the base member; and
      a measuring element deposited over the surface of the base member and the surface of the insulating member, a portion of the measuring element directly contacting the base member.

2. The sample for electron microscopy according to claim 1, wherein the insulating member is made of ceramic or glass.

3. The sample for electron microscopy according to claim 1, further comprising:
   a terminal device through which a measurement signal generated by the measuring element is extracted to an outside,
   wherein the terminal device includes
      an insulating member deposited on the surface of the base member, and
      a terminal element deposited on the surface of the insulating member.

4. The sample for electron microscopy according to claim 1, further comprising:
   a terminal device through which a measurement signal generated by the measuring element is extracted to an outside,
   wherein the terminal device includes a terminal element attached to a sample holder to hold the sample when observation through the electron microscope is conducted.

5. The sample for electron microscopy according to claim 1,
   wherein the sensor is a temperature sensor.

6. The sample for electron microscopy according to claim 1,
   wherein the measuring element comprises a thin film with a thickness of 1-10 microns.

7. The sample for electron microscopy according to claim 1,
   wherein the sample is configured to be attachable and detachable from a sample holder such that the measuring element directly contacts the portion of the base member when the sample is detached from the sample holder.

8. A sample for electron microscopy comprising:
   a base member; and
   a sensor configured to measure data on the sample, the sensor comprising:
      an insulating member deposited in or near an area of observation that is defined on a surface of the base member; and
      a measuring element deposited on a surface of the insulating member, or over the surface of the base member and the surface of the insulating member,
   wherein the sensor comprises a stress sensor configured to measure a stress occurring in the sample,
   wherein the insulating member includes a portion that is free of the measuring element, and
   a recess-filling member is deposited on the portion.

9. The sample for electron microscopy according to claim 8,
   wherein the recess-filling member comprises a film made of a nonmetallic material.

10. The sample for electron microscopy according to claim 8,
    wherein the recess-filling member has a thickness substantially same as a thickness of the measuring element.

11. The sample for electron microscopy according to claim 8,
    wherein the recess-filling member adjoins an edge the measuring element with no gaps interposed therebetween.

12. A method of manufacturing a sample for electron microscopy, the method comprising:
    providing a sensor on a surface of the sample, the sensor being configured to measure data on the sample, the providing of the sensor including
       depositing an insulating member on a surface of a base member included in the sample; and
       depositing, by vacuum deposition, a measuring element on a surface of the insulating member or over the surface of the base member and the surface of the insulating member.

13. The method of manufacturing a sample for electron microscopy according to claim 12,
    wherein the insulating member is deposited by vacuum deposition.

14. The method of manufacturing a sample for electron microscopy according to claim 12, further comprising:
    depositing a recess-filling member,
    wherein a portion of the measuring element directly contacts the base member.

15. The method of manufacturing a sample for electron microscopy according to claim 12,
    wherein the measuring element comprises a thin film with a thickness of 1-10 microns.

16. A method of manufacturing a sample for electron microscopy, the method comprising:
    depositing an insulating member on a surface of a base member included in the sample; and
    depositing, by vacuum deposition, a measuring element on a surface of the insulating member, or over the surface of the base member and the surface of the insulating member to provide a sensor on a surface of the sample, the sensor being configured to measure data on the sample.

17. The method of manufacturing a sample for electron microscopy according to claim 16,
    wherein the insulating member is deposited by vacuum deposition.

18. The method of manufacturing a sample for electron microscopy according to claim 16, further comprising:
    depositing a recess-filling member on the portion,
    wherein a portion of the measuring element directly contacts the base member.

19. The method of manufacturing a sample for electron microscopy according to claim 16,
    wherein the measuring element comprises a thin film with a thickness of 1-10 microns.

* * * * *